(12) United States Patent
Moroni et al.

(10) Patent No.: US 6,465,014 B1
(45) Date of Patent: Oct. 15, 2002

(54) PH-DEPENDENT SUSTAINED RELEASE, DRUG-DELIVERY COMPOSITION

(75) Inventors: Antonio Moroni, Morris Plains, NJ (US); William Drefko, Kearny, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/814,084

(22) Filed: Mar. 21, 2001

(51) Int. Cl.[7] ............................ A61K 9/14; A61K 9/20; A61K 9/48; A61K 9/66
(52) U.S. Cl. ..................... 424/486; 424/489; 424/452; 424/455; 424/465
(58) Field of Search .................................. 424/486, 489, 424/452, 455, 465

(56) References Cited

U.S. PATENT DOCUMENTS 5,456,923 A * 10/1995 Nakamichi et al. ......... 424/489

* cited by examiner

*Primary Examiner*—Thurman K. Page
*Assistant Examiner*—Blessing Fubara
(74) *Attorney, Agent, or Firm*—Walter Katz; William J. Davis; Marilyn J. Maue

(57) ABSTRACT

A pH-dependent sustained release, drug delivery composition capable of being formed into tablets or pellets, wherein the release is controlled by a diffusion barrier formed by the interaction of a pH-dependent gelling material and a pH-independent non-gelling material, comprising a polymer matrix comprising, by weight, (a) 10 to 50% sodium alginate, (b) 2 to 15% propylene glycol alginate and (c) 40 to 80% of a pharmaceutical medicament.

9 Claims, No Drawings

PH-DEPENDENT SUSTAINED RELEASE, DRUG-DELIVERY COMPOSITION

BACKGROUND OF THE INVENTION

1. Field of the Invention

This invention relates to pH-dependent sustained release, drug-delivery composition, and, more particularly, to an effective composition which is characterized by including about 20 to 40% by weight of sodium alginate, about 4 to 12% of propylene glycol alginate (PGA), and about 40 to 80% of a pharmaceutical medicament.

2. Description of the Prior Art

U.S. Pat. No. 4,792,452 described a controlled release pharmaceutical formulation was described which released a pharmaceutical of a basic character at a controlled rate regardless of the pH of the environment. The formulation included a basic pharmaceutical, up to about 45% by weight of a pH dependent polymer, which was a salt of alginic acid, such as sodium alginate, and up to 35% by weight of a pH-independent hydrocarbon gelling agent such as hydroxypropylmethyl cellulose, in a 2% solution.

Many other references have described similar formulations in tablet form using a single alginate salt or combinations of salts.

Accordingly, it is an object of this invention to provide a pH-dependent sustained release, drug-delivery composition capable of being formed into tablets or pellets which includes a diffusion barrier formed by the interaction of a pH-dependent gelling material and a pH-independent non-gelling material.

A feature of the invention is the provision of such a composition which will provide a dissolution rate of about 20% of the drug within about 2 hours at acid pH, while the remaining 80% of the drug is released within at least 10 hours at alkaline or neutral pH, preferably 100% of the drug over a period of 12 hours.

SUMMARY OF THE INVENTION

What is described herein is a pH-dependent sustained release, drug delivery composition capable of being formed into tablets or pellets, wherein the release is controlled by a diffusion barrier formed by the interaction of a pH-dependent gelling material and a pH-independent non-gelling material, comprising a polymer matrix which includes, by weight, (a) 10 to 50% sodium alginate, (b) 2 to 15% propylene glycol alginate, and (c) 40 to 80% of a pharmaceutical medicament.

A preferred composition herein includes: (a) 20 to 40%, (b) 4 to 12% and (c) 45–68%.

These compositions will achieve up to a 20–40% dissolution of the medicament within 2 hours, and the remaining 60–80% will achieve dissolution within 10 hours.

DETAILED DESCRIPTION OF THE INVENTION

In accordance with the invention, the composition in the form of tablets or pellets will release a drug within a period of 12 hours.

In this invention, dissolution of poorly water-soluble drugs is controlled by the swelling/erosion properties of the composition; while for water-soluble drugs it is controlled by diffusion through the composition.

In a preferred form of the invention, the sodium alginate component is present in an amount of 20–40% by weight of the composition, the propylene glycol alginate is 4–12%, and the drug is present 45–68%; and dissolution of the drug is accomplished at a release rate of between about 0.175%/min and 0.2%/min.

The formulation herein may optionally be coated with one or more film formers, employing one or more plasticizers, and one or more solvents and other conventional coating ingredients.

A wide variety of medicaments, including basic, neutral and acidic drugs, which ordinarily are orally administered in tablet form can be used in the form of tablets prepared according to this invention. These include, for example, drugs of a basic nature drug such as adrenergic agents such as salts of ephedrine, desoxyephedrine, phenylephrine, epinephrine, salbutamol, terbutaline and the like, cholinergic agents such as salts of physostigmine, neostigmine and the like, antispasmodic agents such as salts of atropine, methantheline, papaverine and the like, curariform agents such as salts of chlorisondamine and the like, tranquilizers and muscle relaxants such as salts of fluphenazine, thioridazine, trifluoperazine, chlorpromazine, triflupromazine and the like, antidepressants like salts of amitriptyline, nortriptyline, and the like, antihistamines such as salts of diphenhydramine, chlorpheniramine, dimenhydrinate, tripelennamine, perphenazine, chlorprophenazine, chlorprophenpyridamine and the like, cardioactive agents such as salts of verapamil, diltiazem, gallapomil, cinnarizine, propranolol, metoprolol, nadolol, and salts of any of the following: antimalarials such as chloroquine and the like, analgesics such as propoxyphene, meperidine and the like, etc. Other neutral and acidic therapeutic agents having the same or different physiological activity can also be employed in pharmaceutical preparations within the scope of the present invention.

Drugs can be in various forms, such as uncharged molecules, components of molecular complexes, or non-irritating pharmacologically acceptable salts, e.g. the hydrochloride, hydrobromide, sulphate, phosphate, nitrate, borate, acetate, maleate, tartarate, salicylate, etc. For acidic drugs, salts of metals, amines, or organic cations (e.g. quaternary ammonium) can be employed. Furthermore, simple derivatives of the drugs (such as ethers, esters, amides, etc.) which have desirable retention and release characteristics but which are easily hydrolyzed by body pH, enzymes, etc., can be employed.

The amount of drug incorporated in the carrier varies widely depending on the particular drug. The desired therapeutic effect, and the time span for which it takes the drug to be released. Since a variety of carriers in a variety of sizes and shapes are intended to provide complete dosage regimen for therapy for a variety of maladies, there is no critical upper limit on the amount of drug incorporated in the carrier. The lower limit, too, will depend on the activity of the drug and the span of its release from the carrier. Thus, it is not practical to define a range for the therapeutically effective amount of drug to be released by the carrier.

Preferred drugs to be incorporated according to the present invention are those designed for long-term treatment so that multiple daily doses can be avoided. For example, smooth muscle relaxants, e.g. theophylline, anabolics, e.g. methandrostenolone; analgesics, e.g. acetylsalicyclic acid, phenylbutazone or methadone; androgens, e.g. methyltestosterone; antibiotics, e.g. rifampin; antidepressants, e.g. imipramine or maprotiline; antidiabetics, e.g. phenformin; anticonvulsives, e.g. cabamazepine, antihistamines, e.g. tripelennamine; antihypertensives, e.g. hydrolazine;

antinmfectives, e.g. trimethoprim; antiparasitics, e.g. nifurimox; antiparkinson agents, e.g. levodopa; antiph logistics, e.g. nap roxen; antitussives, e.g. benzostate; appetite depressants, e.g. mazndol; bronchodilators, e.g. fenoterol; coronary dilators, e.g. fenalcomine; corticoids, e.g. dexamethasone; cytostatics, e.g. floxuridine; diuretics, e.g. hydrochiorothiazide; hypnotics, e .g. glutethimide; neuroleptics, e.g. reserpine or thioridazine; psychoanaleptics, e.g. methylpenidate; tranquilizers, e.g. diazepam; uricosutics, e.g. sulfinpyrazone; vasodilators, e.g. isoproterenol.

Among the most preferred drugs are naproxen sodium, diclofenac sodium, baclofen, metropolol HCl, beta blockers, such as oxprenolol and propranolol; calcium channel blockers, such as Nifedipine and Verapamil, and antiasthmatics, such as theophylline.

The composition optionally can contain excipients such as fillers, lubricants, binders and the like.

EXAMPLE 1

In a typical run, a pH-dependent sustained release drug tablet was prepared using a polymer blend of sodium alginate and propylene glycol alginate yielding a polymer matrix composed of a pH-dependent gelling material and pH-independent non-gelling material, respectively. With propranolol HCl as a model highly water-soluble, weakly basic drug, a drug dissolution rate of 95% was achieved in 12 hours, with the first 2 hours of dissolution completed at pH 1.5, followed by 10 additional hours at pH 7.2. The tableted composition contained 50% of the drug and 35% of the polymer matrix of 30% sodium alginate and 5% propylene glycol alginate. The remaining ingredients were filler, lubricant and binder (such as Plasdone® K-25, K-29/32 or K-90 (polyvinylpyrrolidones)) and S-630 (a vinyl pyrrolidbne-vinyl acetate copolymer).

Suitable compositions of the propanolol HCl drug are given in Table 1 below.

TABLE 1

Propanolol HCl Compositions

| Formulation<br>Component | 1a<br>% | 2a<br>% | 3a<br>% | 4a<br>% |
|---|---|---|---|---|
| Propanolol HCl | 50 | 50 | 50 | 50 |
| Keltone ® HV (sodium alginate) | 30 | — | 20 | — |
| Manugel ® LBA (sodium alginate) | — | 20 | — | 30 |
| PVP K-90 | 2 | 2 | 2 | 2 |
| Kelcoloid ® LVF (propylene glycol alginate) | 6 | 16 | — | — |
| Kelcoloid ® HVF (propylene glycol alginate) | — | — | 16 | 6 |
| Microcrystalline cellulose | 7 | 7 | 7 | 7 |
| Lactose (monohydr.) | 4 | 4 | 4 | 4 |
| Magnesium stearate | 1 | 1 | 1 | 1 |

Granulations were performed in a Uni-Glatt fluid bed granulator. Tableting was performed using a Stokes B2 tablet press equipped with round, flat faced punches 9.5 mm in diameter to obtain tablet hardness of 8–10 Kp. Dissolution studies were conducted in acid (0.1N HCl, pH 1.2) for 2 hours and alkaline (Potassium phosphate buffer, pH 7.2) media at 37° C.

EXAMPLE 2

Similar results were obtained with diclofenac Na, a poorly water-soluble, weakly acidic, drug. Suitable compositions are shown in Table 2 below.

TABLE 2

Diclofenac Na Compositions

| Formulation<br>Component | 1b<br>% | 2b<br>% | 3b<br>% | 4b<br>% |
|---|---|---|---|---|
| Diclofenac Na | 68 | 53 | 60 | 45 |
| Keltone ® HV | 25 | 40 | 25 | 40 |
| PVP K-90 | 2 | 2 | 2 | 2 |
| Kelcoloid ® LVF | 4 | 4 | 12 | 12 |
| Magnesium stearate | 1 | 1 | 1 | 1 |

Granulations were performed similarly to Example 1.

EXAMPLE 3

Theophylline is a poorly water-soluble, neutral bronchodilator drug commercially available in dosages of 100 mg, 200 mg, 300 mg, and 450 mg tablets for oral administration.

A mixture design was conducted to screen three factors, namely:

(A) Keltone® HV level (25% or 40%)
(B) Kelcoloid® LVF level (4% or 1 2%)
(C) Theophylline level (68%, 53%, 60% and 45%)

The formulations were made by mixing followed by direct compression.

TABLE 3

Theophylline Formulations

| Component | I | II | III | IV |
|---|---|---|---|---|
| Theophylline | 68 | 53 | 60 | 45 |
| Keltone ® HV | 25 | 40 | 25 | 40 |
| PVP K-90 | 2 | 2 | 2 | 2 |
| Kelcoloid ® LVF | 4 | 4 | 12 | 12 |
| Colloidal SiO$_2$ | .5 | .5 | .5 | .5 |
| Magnesium stearate | .5 | .5 | .5 | .5 |

Drug release profiles for all the formulations were quite linear; therefore the slope of linear fit (4 hours–10 hours) was estimated as the rate of dissolution for each formulation. The linear dissolution profiles also suggest a release not controlled by diffusion, but rather by swelling/erosion.

What is claimed is:

1. A pH-dependent sustained release, drug delivery composition, wherein the release is controlled by a diffusion barrier formed by the interaction of a pH-dependent gelling material and a pH-independent non-gelling material, comprising a polymer matrix, by weight, (a) 10 to 50% sodium alginate, (b) 2 to 15% propylene glycol alginate and (c) 40 to 80% of a pharmaceutical medicament, which will achieve less than 40% dissolution of the medicament within 2 hours at an acidic pH, and dissolution of the remaining drug at neutral or alkaline pH over a period of at least 10 hours.

2. The composition of claim 1 wherein (a) is 20 to 40%, (b) is 4 to 12% and (c) is 45–68%.

3. The composition of claim 1 wherein said medicament is propranolol HCl.

4. The composition of claim 1 wherein said medicament is diclofenac Na.

5. The composition of claim 1 wherein said medicament is theophylline.

6. The composition of claim 1 wherein said medicament is verapamil.

7. The composition of claim 1 further comprising a binder.

8. The composition of claim 7 wherein said binder is polyvinylpyrrolidone.

9. The composition of claim 7 wherein said binder is a vinylpyrrolidone-vinyl acetate copolymer.

* * * * *